(12) United States Patent
Kratzer et al.

(10) Patent No.: US 7,763,207 B2
(45) Date of Patent: Jul. 27, 2010

(54) THROUGHFLOW DEVICE FOR MEASURING PLATELET FUNCTION OF PRIMARY HEMOSTASIS, AGGREGATION AND/OR COAGULATION AND/OR VISCOSITY OF BLOOD

(75) Inventors: Michael Kratzer, Munich (DE); Volker Von Der Goltz, Seeon (DE)

(73) Assignee: VDG-Von der Goltz GmbH, Seeon (DE)

( * ) Notice: Subject to any disclaimer, the term of this patent is extended or adjusted under 35 U.S.C. 154(b) by 682 days.

(21) Appl. No.: 10/589,034

(22) PCT Filed: Feb. 4, 2005

(86) PCT No.: PCT/DE2005/000196

§ 371 (c)(1),
(2), (4) Date: Oct. 10, 2006

(87) PCT Pub. No.: WO2005/075985

PCT Pub. Date: Aug. 18, 2005

(65) Prior Publication Data

US 2007/0243105 A1    Oct. 18, 2007

(30) Foreign Application Priority Data

Feb. 9, 2004    (DE) .................... 10 2004 006 316

(51) Int. Cl.
*G01N 15/06* (2006.01)
(52) U.S. Cl. ..................................... 422/68.1
(58) Field of Classification Search ............... 422/68.1
See application file for complete search history.

(56) References Cited

U.S. PATENT DOCUMENTS 6,159,741 A * 12/2000 Kratzer et al. ............. 436/69
7,361,306 B2 * 4/2008 Bote Bote .................. 422/73

FOREIGN PATENT DOCUMENTS

| DE | 196 17 407 A1 | 4/1996 |
| DE | 202 12 149 U1 | 8/2002 |
| EP | 0 223 004 A2 | 2/1985 |
| EP | 0 635 720 A2 | 7/1994 |
| WO | WO 99/39182 | 8/1999 |
| WO | WO 03087817 A2 * | 10/2003 |

OTHER PUBLICATIONS

A. Calatzis et al., Point-of-Care Testing of Hemostatic Alterations in Anaesthesia and Intensive Care, Anaesthesist, vol. 52, No. 3, 2003, pp. 229-237.

\* cited by examiner

*Primary Examiner*—Walter D Griffin
*Assistant Examiner*—Bobby Ramdhanie
(74) *Attorney, Agent, or Firm*—Karl F. Milde, Jr.; Eckert Seamans; Cherin & Mellott, LLC

(57) ABSTRACT

The invention relates to a throughflow device for measuring platelet function of primary hemostasis, aggregation and/or coagulation and/or viscosity of the blood. A reservoir (8), from which blood can be taken for measurement and transported through an aperture (7), is arranged in a housing (2). A stirring device (10,11,12,13) is provided in the reservoir (8) and can be moved in such a way that a stirrer part (11) of the stirring device (10,11,12,13) mixes the blood which is located in the storage chamber (8) during measurement and maintains it in a state of motion.

14 Claims, 4 Drawing Sheets

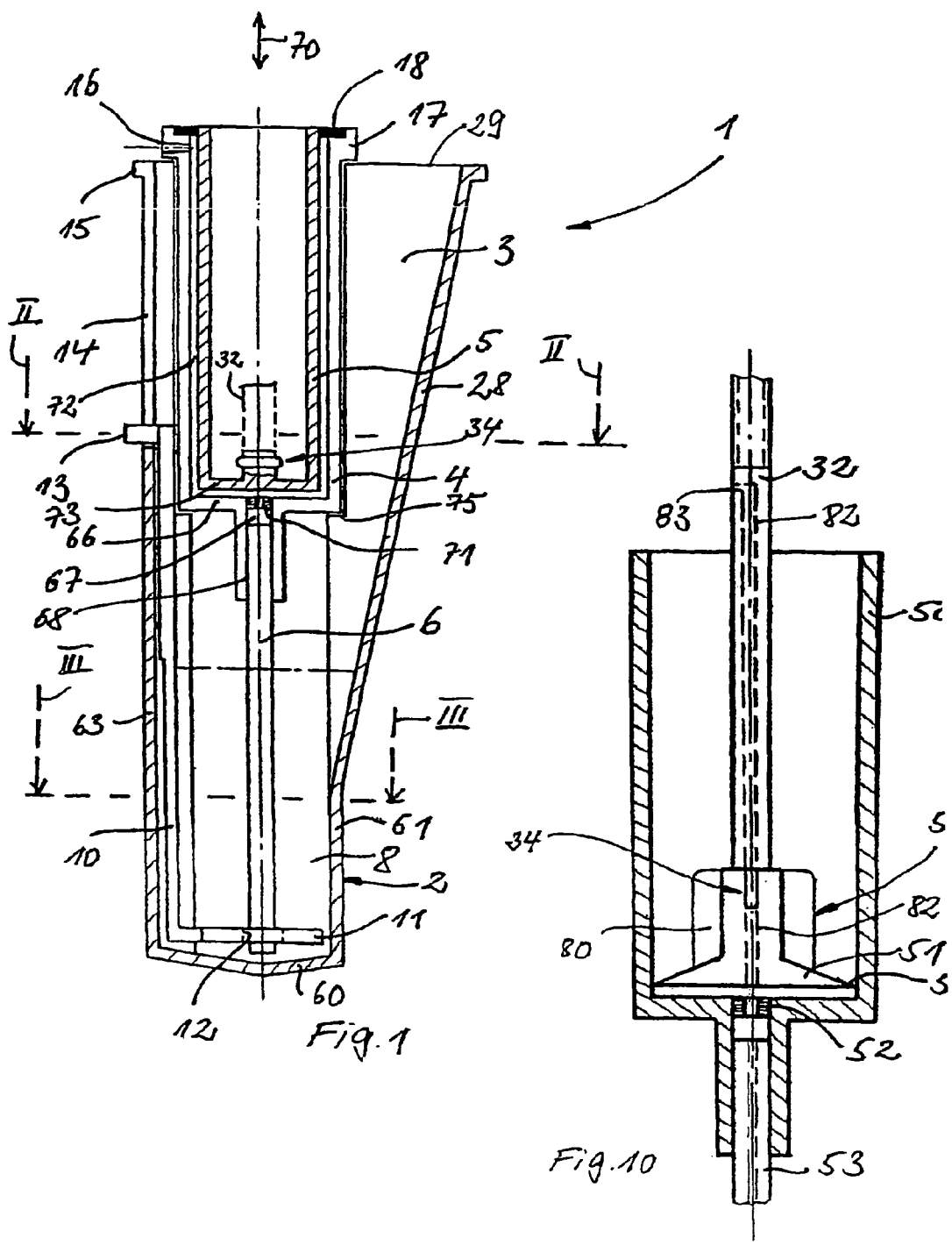

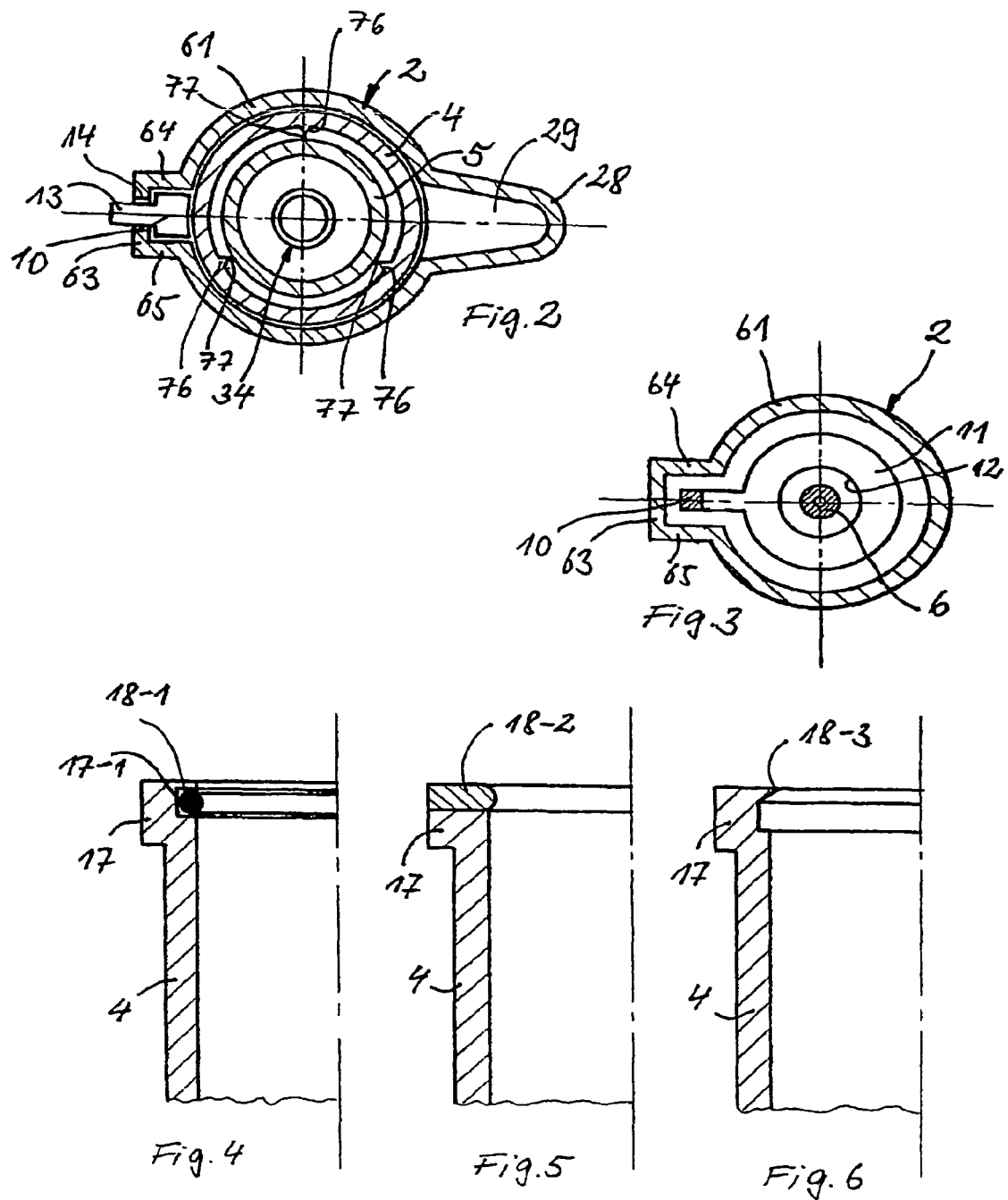

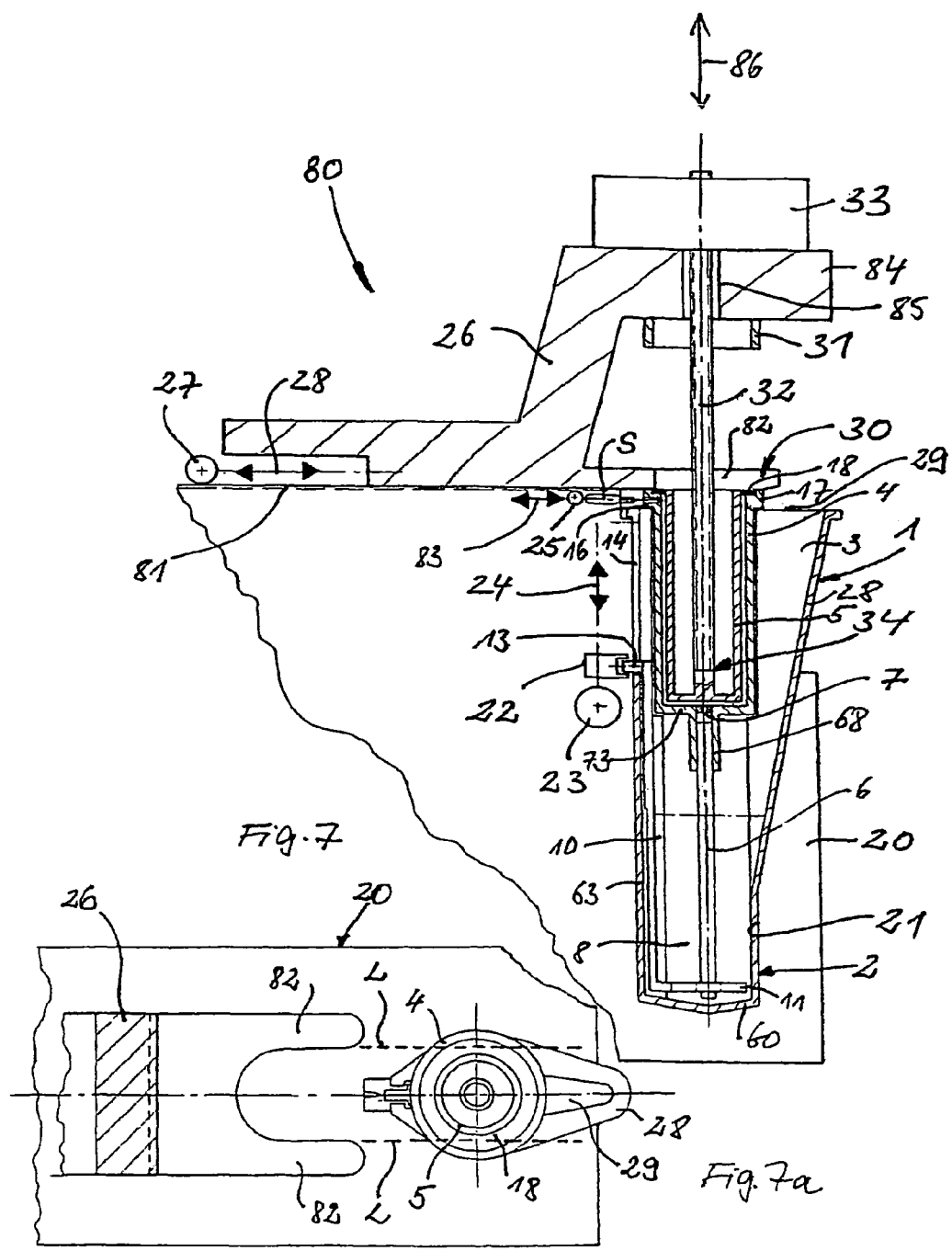

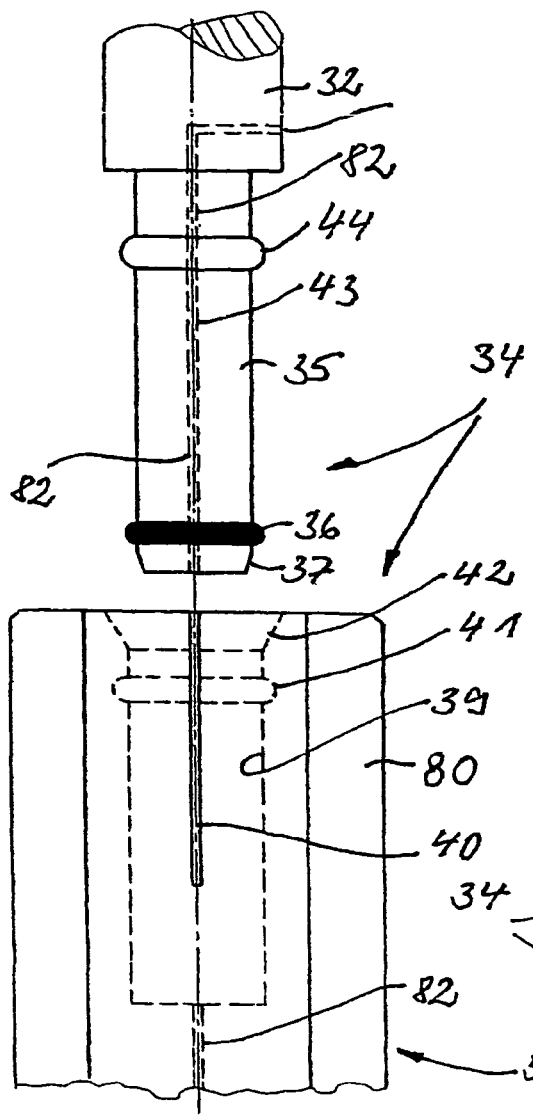
Fig. 8a
Fig. 8b
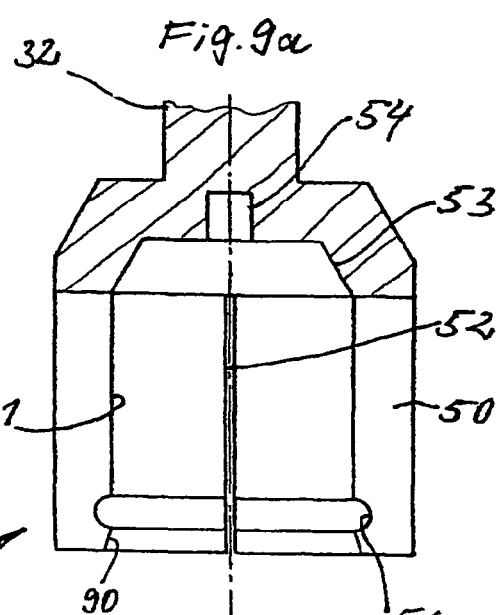
Fig. 9a
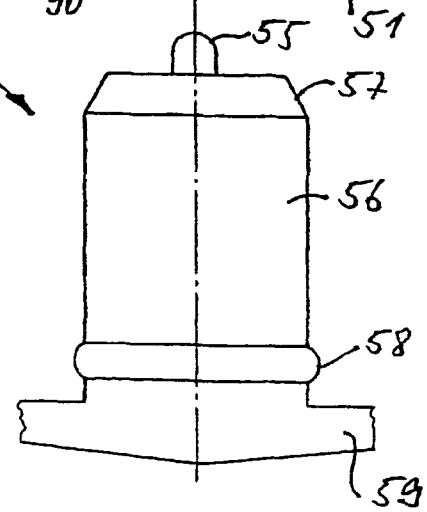
Fig. 9b

THROUGHFLOW DEVICE FOR MEASURING PLATELET FUNCTION OF PRIMARY HEMOSTASIS, AGGREGATION AND/OR COAGULATION AND/OR VISCOSITY OF BLOOD

BACKGROUND OF THE INVENTION

The present invention relates to a flow-through device for measuring the platelet function of primary hemostasis, the aggregation and/or the coagulation and/or the viscosity of the blood, the blood from a blood reservoir being aspirated with the help of a piston, which can be moved in a cylinder, through an aperture and the pressure in the space between the piston and the aspirated blood being measured. At the same time, the piston is moved by a driving mechanism, for example, in such a manner, that a nominal pressure is maintained in the space. The movement of the piston serves then as a measure of the amount of blood flowing through the aperture. Such a device is disclosed in the EP 0 223 044 B1.

SUMMARY OF THE INVENTION

The objective of the present invention is to configure such a device in such a manner, that the carrying out of extremely simple measurements becomes possible without the danger of contamination.

This object, as well as further objects which will become apparent from the discussion that follows, are achieved, in accordance with the present invention, by providing a stirring device arranged in the reservoir and moved in such a manner, that a stirrer part of the stirring device thoroughly mixes the blood in the reservoir during the measurement and keeps it in motion.

The essential advantage of the present invention lies therein that extremely simple measurements of the amount of blood flowing through an aperture of the device in question are possible, because the inventive device is in the form of a disposable part, with which, in each case, only a single measurement is carried out. The danger of contamination therefore does not exist. Measurement errors, attributable to such contamination, can therefore be avoided. The present device, constructed as a disposable part, may be disposed, moreover, extremely simply in a measuring arrangement. For carrying out the measurement, blood can be filled in an extremely simple and rapid manner through a filler opening of the device into the reservoir and the required measurement operations for actuating the piston of the present device as well as the stirring rod of the same, as well as the positioning of the pressure sensor are possible by simply and automatically connecting appropriate driving mechanisms to the device.

A further significant advantage of the present invention lies therein that there is only a very small dead volume between the piston and the cylinder of the present device, so that measurements with very small amounts of blood already are possible.

Since the present device is a disposable part, costly maintenance work and cleaning operations advantageously are not required.

For a full understanding of the present invention, reference should now be made to the following detailed description of the preferred embodiments of the invention as illustrated in the accompanying drawings.

BRIEF DESCRIPTION OF THE DRAWINGS

FIG. 1 partially in section, shows the side view of a preferred embodiment of the inventive device for investigating the aggregation and/or the coagulation and/or the viscosity of the blood.

FIG. 2 shows a section through the inventive device along the line II-II of FIG. 1.

FIG. 3 shows a section through the inventive device along the line III-III of FIG. 1.

FIGS. 4 to 6 show different possibilities for making a seal between the piston and the cylinder of the inventive device.

FIG. 7 shows the inventive device disposed in a measuring arrangement, the measuring arrangement having a driving mechanism for moving the tension member of the piston, a driving mechanism for moving the stirring rod, a driving mechanism for positioning the pressure sensor, as well as a driving mechanism for locking and releasing the inventive device in the measuring arrangement by moving a carriage part into a measuring position or into a release position.

FIG. 7a shows a view of the fork part of the carriage part from above, the fork part being in the release position and the measuring position being indicated diagrammatically by a broken line.

FIGS. 8a and 8b show a preferred embodiment of the coupling of the tension member to the piston of the inventive device.

FIGS. 9a and 9b show a further preferred embodiment of the coupling of the tension member to the piston of the inventive device.

FIG. 10 shows a further preferred embodiment of the piston/cylinder arrangement of the inventive device.

DESCRIPTION OF THE PREFERRED EMBODIMENTS

The preferred embodiments of the present invention will now be described with reference to FIGS. 1-10 of the drawings. Identical elements in the various figures are designated with the same reference numerals.

In FIG. 1, the inventive device for measuring the aggregation of the blood platelets or the coagulation of the blood or the viscosity of the blood is labeled 1. It comprises, essentially, a housing 2, a piston 5, a cylinder 4 and a stirring device 10, 11, 12 and 13.

As shown also in FIGS. 2 and 3, the housing 2 is constructed essentially tubularly. It is closed off by a bottom wall 60 at its lower end and is open at its top end. The side wall of the housing 2 is labeled 61. At its upper end, this side wall 61 has a flange 15, which protrudes radially to the outside and surrounds the upper opening of the housing 2.

According to the representation of FIGS. 1 and 2, there is an outwardly curved projection, which is surrounded by the approximately socket-shaped, outwardly inclined side wall region 28, in the side wall 61 at the right side of the housing 2. Due to this curved projection, a filling space 3 is created, which forms a lateral opening region 29, which adjoins the upper opening of the housing 2 and through which the blood may be filled into the housing 2. The blood, filled through the opening region 29, flows downward in the direction of the bottom wall 60 of the housing 2 and collects in the reservoir 8 located ahead of the bottom wall 60.

At a different side region of the housing 2, preferably opposite to the filling space 3, the side wall 61 of the housing 2 has a further, preferably rectangular projection, which is formed by the side wall regions 63, 64 and 65, as shown in FIGS. 1, 2 and 3. Moreover, the sidewall region 63 has a slot-shaped opening 14, which extends in the longitudinal direction of the housing 2 approximately over the length of the upper third of the housing 2. The function of this further projection 63 to 65 and of the slot-shaped opening 14 will be explained in greater detail later on.

In the interior of the housing 2, there is a tubular cylinder 4, which, at its upper open end, has a ring-shaped flange 17, which protrudes radially to the outside and rests on the upper edge of the tubular housing 2. Preferably, the cylinder 4 and the housing each have a cross-section in the shape of an annulus. The cylinder 4 is closed off at the lower end by a bottom wall 66, which is connected in a known manner with a small suction tube 6, which protrudes into the reservoir 8 and terminates shortly before the bottom wall 60 of the housing 2. The small suction tube 6 is in operative connection with an opening 67, which is disposed in the bottom wall 66 of the cylinder 4 and, in turn, is connected over an aperture 7 with the interior of the cylinder 4. Moreover, the aperture 7 may be disposed in an aperture holder 71, which is inserted tightly in the opening 67. Preferably, the bottom wall 66 has a projection 68, which adjoins at the opening 67, is in the shape of an annulus and forms an elongation of the opening 67 and in which the end of the small suction tube 6, averted from the bottom wall 60, is inserted.

It is pointed out that the small suction tube 6 may also have a very small diameter for certain measurement purposes, so that it forms a capillary resembling a blood vessel.

In the interior of the cylinder 4, there is a piston 5, which can be moved in the direction of arrow 70, that is, in the longitudinal direction of the vessel 2. The outer wall of the piston 5, which preferably also has a cross section in the shape of an annulus, is sealed with respect to the inner wall of the cylinder 7. The diameter of the piston 5 is such that there is a relatively small gap 72 between its outer wall and the inner wall of the cylinder 17. Preferably, the piston 5 is hollow and closed off at its lower end by a bottom wall 73.

The space between the piston 5 and the cylinder 4, corresponding to the gap 72, is connected at the upper end of the cylinder 4 with an opening 16, which preferably is disposed in the region of the flange 17 of the cylinder 2 and serves in a manner still to be explained in greater detail for measuring the pressure existing in said space.

At the side of the bottom wall 73 of the piston 5, averted from the bottom wall 66 of the cylinder 4, there is a coupling part 34, which, in a manner still to be explained in greater detail, may be connected mechanically with a tension member, which is not shown in FIG. 1, for moving the piston 5 in the direction of arrow 70.

The stirring device 10, 11, 12 and 13, which has already been mentioned above, will be described in greater detail in the following. It consists essentially of a lower stirrer part 11, which preferably is in the shape of a washer, and a stirring rod 10, which extends in the longitudinal direction of the housing 2 in the curved projection 63, 64 and 65 and, at its upper end, has a step part 13, which protrudes through the slot-shaped opening 14 radially to the outside over the side wall region 63 and with which the stirring rod 10 can be moved up and down parallel to the arrow 70. The stirrer part 11 extends preferably perpendicularly to the longitudinal direction of the housing 2 and, approximately centrally, has a passage opening 12, through which the capillary 6 extends. In this way, by moving the stirring rod 10, the stirrer part 11 can be moved up and down in the direction of the arrow 70 in the reservoir 8 for mixing the blood contained in the reservoir, as will be explained later on in greater detail.

With the edge region of its bottom wall 76, the cylinder 4 is seated on a shoulder 75, formed in the housing 2, and is firmly connected with the housing 2.

In order to make an accurate and play-free guidance of the piston 5 in the cylinder 4 possible, bridges 76 are provided, which preferably are distributed uniformly over the periphery of the inner wall of the cylinder 4, extend in each case in the longitudinal direction and, starting out from the inner wall of the cylinder 4, extend in the direction of the outer wall of the piston 5, each bridge 76 preferably forming a peak 77, which is supported at the outer wall of the piston 5. Alternatively, the bridges may also be provided at the piston, in which case they are supported at the cylinder.

It has already been pointed out that the piston 5 is sealed with respect to the cylinder 4 by a ring-shaped sealing device 18, which is shown diagrammatically and FIG. 1. Various sealing arrangements 18-1, 18-2 and 18-3 are now explained in the following in connection with FIGS. 4, 5 and 6.

In accordance with FIG. 4, the sealing arrangement 18-1 has the shape of an O ring seal, which is disposed in an inner groove 17-1 of the flange 17 or of the upper edge of the piston 4.

FIG. 5 shows an embodiment, for which the sealing arrangement 18-2 is a sealing part, which consists of a soft material, is integrally molded in the so-called duplex method to the upper surface of the flange 17, consisting of a comparatively hard material, or of the upper edge of the piston 4 and consists, for example, of a silicon material, which has been compounded with graphite. In the duplex method, the piston 4, with the flange 17 and the sealing arrangement 18-2 are produced in one and a same pressing operation.

According to FIG. 6, it is also conceivable that the sealing arrangement 18-3 has the shape of a ring-shaped sealing lip, which is integrally molded to the inner side of the flange 17 and consists of the material of the piston 4 or of the flange 17.

It is pointed out that it is an essential distinguishing feature of the present invention that the above-described device 1 is in the form of a disposable part. This has the advantage that cleaning operations are not required when carrying out measurements, since each device is used only once for carrying out a measurement. Contaminations and errors in measurement, attributable to defective cleaning operations, can therefore be avoided.

Polyethylene, in particular, is suitable as the material for the device 1, which preferably is produced by an injection molding process.

A measuring arrangement 80 for carrying out a measurement with a device 1 is now explained in greater detail in the following.

In a frame or a housing body 20 or the like, the measuring arrangement 80 has an accommodating space 21 for accommodating device 1, the accommodating space 21 preferably being constructed complementarily to the external contour of the device 1, so that the latter can be inserted automatically only in the correct position in the accommodating space 21. Accordingly, the accommodating space 21 also has accommodating regions for the curved projections 28 and 63, 64, 65.

The measuring arrangement 90 comprises four different driving mechanisms, namely a first driving mechanisms 33 for moving a tension member 32, which can be connected with the piston 5, a second driving mechanisms 23 for moving the stirring device 10 to 13, a third driving mechanism 25 for moving or positioning a pressure sensor S and a fourth driving mechanism 27 for moving a carriage part 26. Moreover, the carriage part 26 and the first driving mechanisms 33, as well as the tension member 32, which can be actuated by the latter, can be moved by the fourth driving mechanism 27 into a measuring position, in which the tension member 32 may be connected mechanically with the piston 5, and into a release position, in which the piston 5 and the tension member 32 are moved upward and separated from one another and the device 1 can be removed from the accommodating space 21.

The carriage part 26 can be shifted preferably horizontally by the fourth driving mechanism 27 in the direction of arrow 28 between said measuring position and the release position. The carriage part 26 has a fork-shaped part 30, which, in the measuring position, is pushed over the device 1 in the accommodating space 21 in such a manner, that especially the inner edges of the fork parts 82, which can be seen in FIG. 7a, are supported at the upper side of the flange 17 of the cylinder 4, so that the upward motion of the cylinder 4 is effectively avoided when, in the measuring position, the piston 5 is pulled upward through the recess, enclosed by a fork parts 82, by moving the tension member 32 upward, as will be explained later on in greater detail. In the measuring position, the axes of the tension member 32 and of the piston 5 are aligned toward one another so that, as a result of the downward motion of the tension member 32, an automatic coupling of the tension member 32 to the piston 5 can take place in the coupling device 34, as will be explained later on in greater detail.

When the device 1 is inserted in the accommodating space 21, it is fixed, so that it cannot twist, in such a manner, that the above-mentioned opening 16 is aligned automatically to the movement direction, indicated by the arrow 83, of a pressure sensor S, moved by the driving mechanism 25, so that the sensor S can be moved completely and tightly by the driving mechanism 25 into the opening 16 for measuring the pressure existing in the space between the cylinder 4 and the piston 5.

At the carriage 26, above of the fork arms 82 of the fork part 30, there is a holding part 84, which has a stepper motor 33 as driving mechanism 33 for moving the tension member 32. The stepper motor 33 can move the tension member 32, which preferably is guided by a borehole 85 of the holding part 84, upward and downward in the direction of arrow 86. The lower end of the tension member 32 can be connected mechanically with the piston 5 in the measuring position or separated from this piston by the coupling device 34, which is shown diagrammatically in FIG. 7.

FIGS. 8a, 8b and 9a, 9b show preferred embodiments of this coupling device.

According to FIG. 9a, a hood-like coupling part 50, which is hollow on the inside and the lower side of which is divided into two halves by a slot extending in the longitudinal direction, is integrally molded to the lower end of the tension member 32. The lower end of the cavity, surrounded by the hood-like coupling part 50, has a region 90, which tapers conically towards the inside and serves as entrance incline for a further coupling part 56, which is fastened to the piston 5. The conical region 90, tapering obliquely to the rear, changes over into a cylindrical region 91, which extends approximately over the length of the slot 52. In the transition region between the conically tapering region 90 and the cylindrical region 91, an internal groove 51, disposed in the inner wall of the hood-shaped coupling part 50, is provided and preferably has a semicircular shape. At its side averted from the conically tapering region 90, the cavity of the hood-shaped coupling part 50 ends in a central depression 54, which can be engaged by a central protrusion 55 of the coupling part 56 of the piston 5. Preferably, in the transition region between the cylindrical region 91 and the central depression 54, there is a region 53, which tapers conically towards the central region 54 and is constructed complementarily to a conical region 57 of the second coupling part 56 of the piston 5. When the first coupling part 50 of the tension member 32 is moved over the second coupling part 56 of the piston 5, the protrusion 55 and the conical region 57 of the second coupling part 56 initially engage the cavity of the first coupling part 50, until a ring-shaped protrusion 58, which protrudes radially above the cylindrical region of the second coupling part 56, reaches the conical region 90 serving as access incline. Because of the arrangement of the slot 52, the first coupling part 50 expands so far and until the ring-shaped protrusion 58 of the second coupling part 56 snaps into the ring-shaped inner groove 51 of the first coupling part 50, the central protrusion 55 then being disposed in the central depression 54 and the conical regions 53 and 57 then lying in contact with one another.

When the first coupling device 50 is pulled from the second coupling device 56 in the reverse direction of motion, the hood-shaped first coupling part 50 expands so far because of the slot 52, that the ring-shaped protrusion 58 is pulled out of the inner groove 5'. The coupling parts 50 and 56 are than separated from one another.

It is pointed out that the embodiment of the coupling device 34 of FIGS. 9a and 9b is suitable especially for the device 1 of FIG. 1.

In the following, in conjunction with FIG. 10, a further embodiment of the piston/cylinder arrangement of the present device 1 is explained in greater detail, the cylinder 50, the aperture holder 52 and a small suction tube 53 being constructed corresponding to the embodiment of FIG. 1. A piston 54 can be moved in the interior of the cylinder 50. The piston 54 consists essentially of a piston part 51 with an integrated sealing lip 55 at the periphery of the piston part 51. At the side of the piston 54, averted from the aperture 52, a step 80, which can be connected over the diagrammatically shown coupling device 34 with the tension member 32, is integrally molded to the piston part 51. The particularly simple configuration of the piston 54 with the integrated sealing the 55 is an advantage of this embodiment. In order to be able to measure the pressure, which exists in the space between the piston 54 and the cylinder 50, a borehole 82, which is shown in FIG. 10 by broken lines and ends in an opening 53, which can be connected tightly with a pressure sensor, extends through the piston part 51 and the step 80 as well as over the coupling device 34 and through the tension member 32.

In conjunction with FIGS. 8a and 8b, a coupling device 34 is now explained, which is suitable particularly for the embodiment of the piston/cylinder arrangement of FIG. 10. In this connection, a cylindrical cavity 39 is disposed in the step 80, the end region of the step 80 being divided preferably into two halves by a slot 40, which extends in the longitudinal direction. At the end facing the rod part 32, the cylindrical cavity 39 the cylindrical cavity 39 changes over into a conically expanded opening region 42, ahead of which there is a ring-shaped inner groove 41, which preferably has a semicircular cross section.

At the end of the tension member 32, a protrusion part 35 is provided which, at the end region facing the step 80 of the piston 54, has a conically tapering and 37, which functions as an entrance incline. A ring-shaped seal 36, which preferably is seated in a ring-shaped depression of the protrusion part 35, is disposed behind the conically tapering region 37. At the protrusion part 35, there is a ring-shaped protrusion 44, which is constructed complementarily to the inner groove 41 of the step 80 and, in the longitudinal direction, is at a distance from the sealing arrangement 36. When the tension member 32 is moved in the direction of the piston 54, the front end of the protrusion part 35 with the seal 36 initially reaches the cylindrical cavity 39 of the step 80, the conical regions 37 and 42 acting as entrance inclines. Upon further movement, the protrusion part 35 is pushed into the cylindrical cavity 39 until the ring-shaped protrusion 44, over the region serving as entrance incline, reaches the cylindrical cavity 39, the end region of the step 80, divided by the slot 40, expanding elastically until the ring-shaped protrusion 44 engages the inner groove 41. A tight connection between the protrusion part 35 and the step 38 is then produced by the seal 36.

Upon movement of the rod part 32 in the reverse direction, if the piston 54 remains stationary, the end region of the step 80 expands elastically because of the arrangement of the slot 40. At the same time, the ring-shaped protrusion 44 of the protrusion part 35 can be pulled out of the inner groove 41 of the step 80, in order to separate the rod part 32 from the piston 54. The regions of the borehole 82, which are disposed, on the one hand, in the rod part 32 and in the protrusion part 35 and, on the other, in the step 80 and the coupling part 51 and which were described already in connection with FIG. 10, are connected tightly with one another by the arrangement of the seal 36 in the cylindrical body 39 when the rod part 32 is coupled to the piston 54.

In conjunction with FIG. 7, the carrying out of a measurement is described in greater detail in the following with the help of the device 1, which is constructed as a disposable part.

To begin with, when the carriage part 26 is in the release position, that is, when it has been moved to the left in FIG. 7 by the driving mechanism 27, so that the fork arms 82 release the accommodating space 21, a device 1 is inserted in the accommodating space 21 of the housing body 20 (FIG. 7a).

Subsequently, the driving mechanism 21 is operated in such a manner, that the carriage part 26 is moved to the right in the direction of arrow 28 into the measuring position, that is, to the rights in FIGS. 7, 7a in such a manner, that the cylinder 4 of the device 1 is fixed by the fork arms 82 to prevent any movement in the longitudinal direction, that is, in the upward direction. This is shown in FIG. 7a by the broken lines L.

Subsequently, blood is filled through the opening region 29 and the filling space 3 into the device 1, the blood subsequently flowing into the reservoir 8 of the device 1.

By actuating the driving mechanism 25, the pressure sensor S is connected tightly with the opening 16 for measuring the pressure existing in the space between the piston 5 and the cylinder 4.

The tension member 33 is moved downward by the driving mechanism 33 until the coupling device 34 automatically produces a mechanical connection between the tension member 32 and the piston 5.

Subsequently, by actuating the driving mechanism 33 for carrying out the measurement, the tension member 32 is moved upward, blood being aspirated from the reservoir 8 by way of the small suction pipe 6 through the aperture 7. The pressure, existing in a space between the piston 5 and the cylinder 4, is measured continuously with the help of the sensor S as a measure of the blocking or clogging of the aperture 7.

By actuating the driving mechanism 23, the stirring rod 10 is moved back and forth continuously in the direction of arrow 24 in the longitudinal direction of the device 1, the blood in the reservoir 8 being mixed continuously by the movement of the stirrer part 11 and kept in motion. It is pointed out that a temperature-controlling device is provided in the housing body 20 and keeps the blood in the reservoir 8 at a specified temperature during the whole of the measurement.

At the end of the measuring operation, the piston 5 is moved upward by the tension member 32 by actuating the driving mechanism 33, until it comes to rest against the stock part 31 of the carriage part 2. Upon further movement of the tension member 32 in the upward direction, the coupling device 34 is opened, so that the piston 5 is separated automatically from the tension member 32.

By actuating me driving mechanism 37, the carriage part 26 is then moved into the release position, the upper edge of the cylinder 4 is released and the device 1 can be removed from the accommodating space 21 (FIG. 7a).

In general, the present invention relates to a flow-through device for measuring the platelet function of primary hemostasis, the aggregation and/or the coagulation and/or the viscosity of blood, a reservoir 8 for blood, from which blood may be taken for measurement and conveyed through an aperture 7, being disposed in a housing 2. A stirring device is provided in the reservoir 8 and can be moved so that a stirrer part 11 of the stirring device mixes the blood in the reservoir 8 during the measurement and keeps it in motion.

It is particularly advantageous if the stirrer part 11, in the region of the blood supply, that is, in the reservoir 8, has no contact with the stationary surfaces of the surrounding walls or the like. By these means, it can be prevented that blood cells or other components of the blood can be damaged or squeezed. Such damage or squeezing could lead to undesirable release of substances, which could lead to a distortion of the result of the measurements.

There has thus been shown and described a novel flow-through device which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A flow-through device for measuring the platelet function of primary hemostasis, the aggregation and/or the coagulation and/or the viscosity of the blood, with a reservoir, which is disposed in a housing and from which blood can be taken for the measurement and conveyed through an aperture, said device comprising a stirring device arranged in the reservoir and moved in such a manner, that a stirrer part of the stirring device thoroughly mixes the blood in the reservoir during the measurement and keeps it in motion, wherein the stirrer part of the stirring device in the reservoir is disposed on a stirring rod, which extends in the longitudinal direction of the housing and can be moved in the longitudinal direction of the housing by a driving mechanism; wherein the stirring device, in the region of the blood supply of the reservoir, has no contact with stationary surfaces of the wall surroundings of the reservoir, so that squeezing of blood cells or other components of the blood can be prevented and substances, which are undesirably released and could lead to distortion of the results of the measurements, do not reach the blood; and wherein the housing has a cylinder and a piston disposed therein, and wherein the aperture is disposed in a bottom wall of the cylinder through which the blood from the reservoir can be passed during a corresponding movement of the piston.

2. The device of claim 1, wherein the stirrer part has the shape of a circular disk.

3. The device of claim 2, wherein the housing has an opening region, through which the blood can be supplied to the reservoir of the housing.

4. The device of claim 3, wherein the opening region is in the shape of a curved projection of the housing, which is surrounded by the socket-shaped, outwardly inclined side wall region of the housing.

5. The device of claim 2, wherein the stirrer part extends essentially perpendicularly to the longitudinal direction of the housing.

6. The device of claim 1, wherein the stirring rod, at its side averted from the stirrer part, has a step part, which protrudes through a slot-shaped opening, which extends in the longitudinal direction of the housing, radially to the outside and can be moved by the driving mechanism, so that the stirrer part can be moved back and forth in the longitudinal direction of the housing in the interior of the reservoir.

7. The device of claim 6, wherein the housing has a curved projection, which extends in the longitudinal direction of the housing and opens up into the reservoir, wherein the stirring rod is disposed in the curved projection in the region of the reservoir and wherein a slot-shaped opening is disposed in the curved projection and above the reservoir.

8. The device of claim 7, wherein the curved projection has a rectangular cross section.

9. The device of claim 7, wherein the curved projection is disposed opposite to a further projection formed in an opening region, through which blood can be supplied to the reservoir of the housing.

10. The device of claim 1, wherein said device is constructed as a disposable part.

11. The device of claim 1, wherein the stirrer part of the stirring device is mounted and can be moved in the reservoir without contacting the latter.

12. The device of claim 7, wherein the stirring rod of the stirring device is mounted and can be moved in the curved projection without contacting it.

13. A flow-through device for measuring the platelet function of primary hemostasis, the aggregation and/or the coagulation and/or the viscosity of the blood, with a reservoir, which, is disposed in a housing and from which blood can be taken for the measurement and conveyed through an aperture, said device comprising (a) a small suction tube or a capillary, which extends into the reservoir preceding the aperture, wherein the blood can be conveyed from the reservoir through the small suction tube or the capillary to the aperture and (b) a stirring device arranged in the reservoir and moved in such a manner, that a stirrer part of the stirring device thoroughly mixes the blood in the reservoir during the measurement and keeps it in motion, wherein the stirrer part of the stirring device in the reservoir is disposed on a stirring rod, which extends in the longitudinal direction of the housing and can be moved in the longitudinal direction of the housing by a driving mechanism, and wherein the stirring device, in the region of the blood supply of the reservoir, has no contact with stationary surfaces of the wall surroundings of the reservoir, so that squeezing of blood cells or other components of the blood can be prevented and substances, which are undesirably released and could lead to distortion.

14. The device of claim 13, wherein the small suction tube or the capillary extends through the opening of the stirrer part.

\* \* \* \* \*